US007195016B2

United States Patent
Loyd et al.

(10) Patent No.: US 7,195,016 B2
(45) Date of Patent: Mar. 27, 2007

(54) TRANSTRACHEAL OXYGEN STENT

(75) Inventors: James Loyd, Nashville, TN (US); Dennis Creedon, Sandwich, MA (US); Lewis H. Marten, Westwood, MA (US)

(73) Assignee: E. Benson Hood Laboratories, Pembroke, MA (US)

( * ) Notice: Subject to any disclaimer, the term of this patent is extended or adjusted under 35 U.S.C. 154(b) by 207 days.

(21) Appl. No.: 10/752,936

(22) Filed: Jan. 7, 2004

(65) Prior Publication Data

US 2005/0145252 A1 Jul. 7, 2005

(51) Int. Cl.
*A61M 16/00* (2006.01)

(52) U.S. Cl. .......................... 128/207.14; 128/200.26; 128/200.24

(58) Field of Classification Search ........... 128/207.14, 128/207.15, 207.17, 207.29, 200.26, 912, 128/DIG. 26; 623/9
See application file for complete search history.

(56) References Cited

U.S. PATENT DOCUMENTS

| | | | | |
|---|---|---|---|---|
| 3,137,299 A * | 6/1964 | Tabor | .................... | 128/207.16 |
| 3,659,611 A * | 5/1972 | Miller | .................... | 128/207.15 |
| 3,693,624 A * | 9/1972 | Shiley et al. | .......... | 128/207.15 |
| 3,973,569 A * | 8/1976 | Sheridan et al. | ........ | 128/207.15 |
| 4,040,428 A * | 8/1977 | Clifford | ................. | 128/207.16 |
| 4,246,897 A * | 1/1981 | Muto | .................... | 128/207.15 |
| 4,325,366 A * | 4/1982 | Tabor | .................... | 128/207.16 |
| 4,332,245 A * | 6/1982 | Boone, Sr. | ............. | 128/207.17 |
| 4,340,046 A * | 7/1982 | Cox | ...................... | 128/207.17 |
| 4,435,853 A * | 3/1984 | Blom et al. | ..................... | 623/9 |
| 4,488,545 A * | 12/1984 | Shen | ..................... | 128/207.29 |
| 4,596,579 A * | 6/1986 | Pruitt | ............................ | 623/9 |
| 4,614,516 A * | 9/1986 | Blom et al. | ..................... | 623/9 |
| 4,649,913 A | 3/1987 | Watson | | |
| 4,817,598 A * | 4/1989 | LaBombard | .......... | 128/207.14 |
| 4,820,304 A * | 4/1989 | Depel et al. | .................... | 623/9 |
| 4,911,716 A * | 3/1990 | Blom et al. | ..................... | 623/9 |
| 4,964,850 A * | 10/1990 | Bouton et al. | .............. | 604/540 |
| 4,966,141 A * | 10/1990 | Bacaner et al. | ........ | 128/207.14 |
| 5,017,188 A * | 5/1991 | Marten et al. | .............. | 604/178 |
| 5,042,475 A * | 8/1991 | LaBombard | ........... | 128/207.14 |
| 5,054,482 A * | 10/1991 | Bales | .................... | 128/207.14 |
| 5,058,580 A * | 10/1991 | Hazard | .................. | 128/207.15 |
| 5,188,100 A * | 2/1993 | Miles et al. | ........... | 128/207.14 |
| 5,207,652 A * | 5/1993 | Kay | ........................... | 604/180 |
| 5,224,935 A * | 7/1993 | Hollands | .................... | 604/180 |
| 5,251,617 A * | 10/1993 | Linder | .................... | 128/200.26 |
| 5,259,376 A * | 11/1993 | Bales | .................... | 128/207.17 |
| 5,287,852 A * | 2/1994 | Arkinstall | ............... | 128/207.14 |
| 5,300,119 A * | 4/1994 | Blom | ............................ | 623/9 |
| 5,305,740 A * | 4/1994 | Kolobow | ............... | 128/207.14 |
| 5,419,314 A * | 5/1995 | Christopher | ........... | 128/200.26 |
| 5,471,980 A | 12/1995 | Varner | | |
| 5,474,544 A * | 12/1995 | Lynn | ............................ | 604/537 |
| 5,494,029 A | 2/1996 | Lane et al. | | |

(Continued)

*Primary Examiner*—Teena Mitchell
*Assistant Examiner*—Annette Dixon
(74) *Attorney, Agent, or Firm*—Frommer Lawrence & Haug LLP; Ronald R. Santucci

(57) ABSTRACT

An apparatus and method for implanting a surgical apparatus including a first flange having an opening, a second flange having an opening, and a shaft having a lumen connecting the first and second flange openings. The surgical apparatus is inserted into a stoma formed in the trachea of a patient. The surgical apparatus receives and secures an oxygen supply line for patients who have difficulty breathing.

19 Claims, 2 Drawing Sheets

U.S. PATENT DOCUMENTS

| | | | | |
|---|---|---|---|---|
| 5,507,809 A * | 4/1996 | Blom | | 623/9 |
| 5,515,844 A * | 5/1996 | Christopher | | 128/200.26 |
| 5,529,062 A | 6/1996 | Byrd | | |
| 5,558,081 A * | 9/1996 | Lipkin | | 128/200.24 |
| 5,571,180 A * | 11/1996 | Blom | | 623/9 |
| 5,578,083 A * | 11/1996 | Laguette et al. | | 623/9 |
| 5,616,116 A | 4/1997 | Born | | |
| 5,671,732 A | 9/1997 | Bowen | | |
| 5,738,095 A | 4/1998 | Persson | | |
| 5,762,638 A * | 6/1998 | Shikani et al. | | 604/265 |
| 5,782,236 A * | 7/1998 | Ess | | 128/207.17 |
| 5,819,734 A | 10/1998 | Deily et al. | | |
| 5,833,666 A * | 11/1998 | Davis et al. | | 604/180 |
| 5,839,437 A | 11/1998 | Briggs, III | | |
| 5,840,091 A | 11/1998 | Strong | | |
| 5,897,531 A * | 4/1999 | Amirana | | 604/180 |
| 5,935,165 A * | 8/1999 | Schouwenburg | | 623/9 |
| 5,957,978 A | 9/1999 | Blom | | |
| 5,983,895 A | 11/1999 | Turner | | |
| 6,053,167 A | 4/2000 | Waldeck | | |
| 6,105,573 A | 8/2000 | Delaplane et al. | | |
| 6,105,577 A | 8/2000 | Varner | | |
| 6,135,110 A | 10/2000 | Roy | | |
| 6,394,092 B1 | 5/2002 | Barrett et al. | | |
| RE38,145 E * | 6/2003 | Lynn | | 604/537 |
| 6,612,305 B2 * | 9/2003 | Fauza | | 128/200.26 |
| 6,635,022 B2 * | 10/2003 | Berg et al. | | 600/585 |
| 6,637,435 B2 | 10/2003 | Ciaglia et al. | | |
| 6,701,928 B2 * | 3/2004 | Rubin et al. | | 128/207.14 |
| 6,706,017 B1 * | 3/2004 | Dulguerov | | 604/164.01 |
| 6,725,862 B2 * | 4/2004 | Klinberg et al. | | 128/207.14 |
| 6,755,191 B2 * | 6/2004 | Bertoch et al. | | 128/200.26 |
| 6,772,758 B2 * | 8/2004 | Lambert | | 128/204.17 |
| 6,776,797 B1 * | 8/2004 | Blom et al. | | 623/14.11 |
| 6,796,309 B2 * | 9/2004 | Nash et al. | | 128/207.14 |
| 6,802,836 B2 * | 10/2004 | Bouphavichith et al. | | 604/534 |
| 6,886,558 B2 * | 5/2005 | Tanaka | | 128/200.26 |
| 2002/0007833 A1 * | 1/2002 | Fauza | | 128/207.15 |
| 2002/0078962 A1 * | 6/2002 | Nash et al. | | 128/207.15 |
| 2002/0092526 A1 * | 7/2002 | Bertoch et al. | | 128/207.17 |
| 2002/0193879 A1 * | 12/2002 | Seder et al. | | 623/9 |
| 2003/0037789 A1 * | 2/2003 | Klinberg et al. | | 128/207.14 |
| 2003/0131853 A1 * | 7/2003 | Wall et al. | | 128/207.14 |
| 2004/0060563 A1 * | 4/2004 | Rapacki et al. | | 128/207.14 |
| 2005/0145252 A1 * | 7/2005 | Loyd et al. | | 128/207.14 |
| 2005/0166924 A1 * | 8/2005 | Thomas et al. | | 128/207.14 |

* cited by examiner

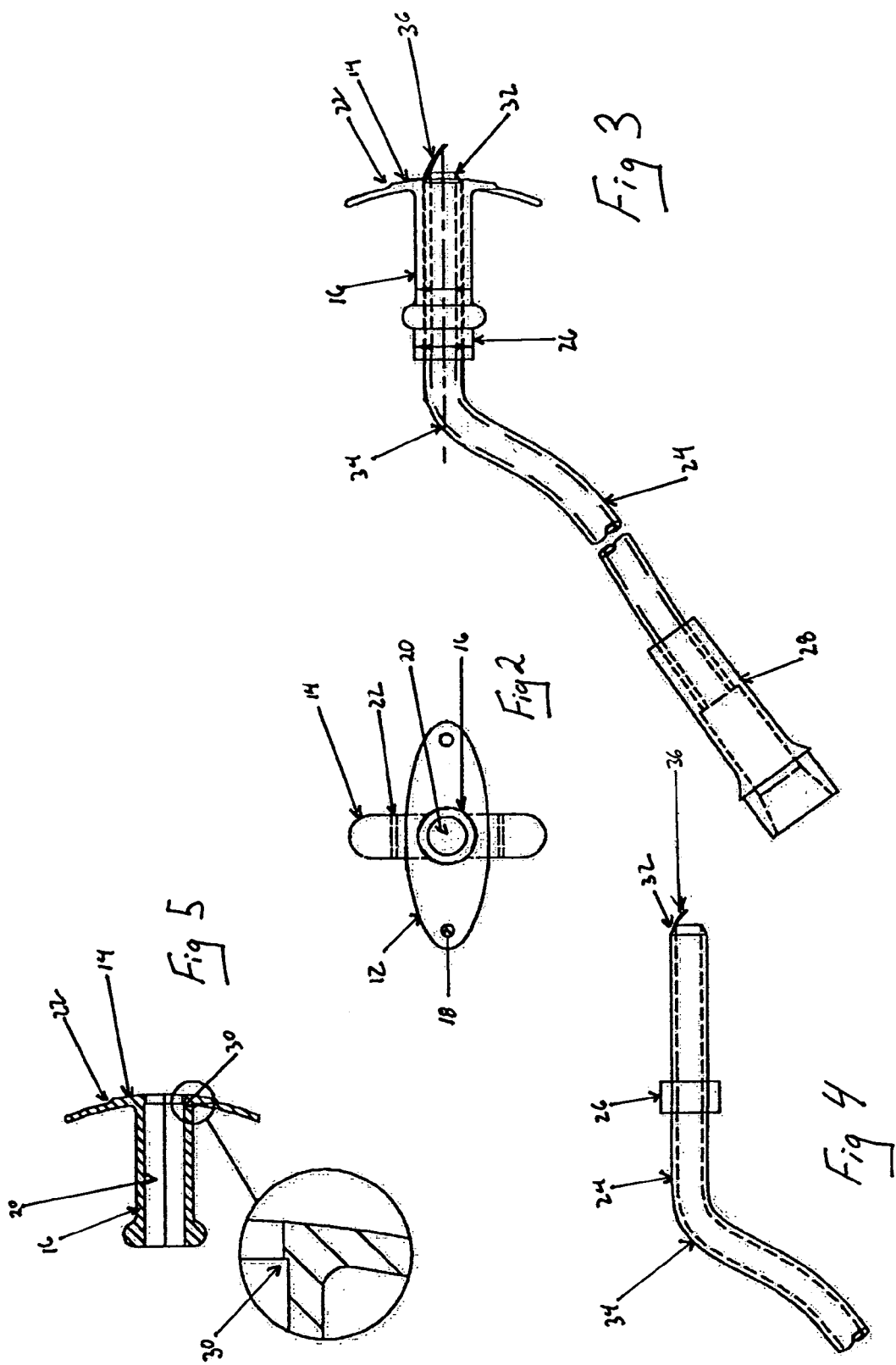

TRANSTRACHEAL OXYGEN STENT

BACKGROUND OF THE INVENTION

1. Field of the Invention

The present invention relates to devices for securing oxygen supplies to a patient. Specifically, the present invention is directed to a transtracheal stent that accepts the insertion of standard oxygen tubing for use with patients suffering from emphysema or other breathing disorders.

2. Description of the Prior Art

There are a wide variety of products and devices which have been described for supplying oxygen to patients. Traditionally, this has been accomplished through the use of an oxygen supply which is adapted to fit over the patients ears and supply oxygen to the patient through the nose. For a variety of reasons this type of application is not desirable. These devices are quite inconvenient and obtrusive into the life of the patient and can become uncomfortable for the wearer. Accordingly, one aspect of the present invention is directed at an oxygen supply device and system which provides for greater comfort and convenience for the user.

Other devices have been developed for implantation into the trachea of a patient. In particular, attention is directed at tracheotomy tubes. These tubes are inserted into the trachea of the patient for a variety of reasons including to promote healing in the patient, permit speaking and breathing following a laryngectomy, provide an access point for forced ventilation of a patient, and a variety of other uses including supplying oxygen to augment normal breathing.

In one example described in U.S. Pat. No. 5,957,978, the tracheotomy tube is equipped with an outer port for permitting air to flow into and out of the tracheotomy tube, an inner port that permits air to flow to and from the lungs once inside the trachea of the patient, and a fenestration with valve to permit the flow of air through the larynx to permit the wearer to speak. The user must occlude the outer port and exhale to force air through the fenestration to permit speaking, and then release the outer port occluder to breath again. As described in the '978 patent the trachea itself is blocked by a balloon which extends laterally off of the tracheotomy tube to prevent objects from entering the lungs and to force the air flow through the tracheotomy tube itself.

Another apparatus in the prior art is the tracheostoma device depicted in U.S. Pat. No. 5,738,095. The device is intended to be manually controlled and has a valve which is use to prevent the egress of air out of a stoma in which it is implanted when it is desired that air should flow through a voice prosthesis which is implanted in a fistula connecting the trachea and the esophagus to enable the user to talk. The device also has air filtration and moisture and heat exchanging functionality. This device is placed in a holder which covers the stoma formed in the patients trachea.

A further example of a tracheostomy tube can be seen in U.S. Pat. No. 6,135,110. The device comprises a tracheostomy tube which can allow for either forced ventilation or the ingress and egress of air by the patient's normal breathing. One aspect of the apparatus described in the '110 patent is the use of both an inner and outer cannula. This enables the inner cannula to be removed from the patient, cleaned, and re-inserted without the need to disturb the outer cannula, which could be uncomfortable for the patient. Further this allows for the use of several types of inner cannula depending upon the application and desired usage. To secure the inner cannula to the outer cannula a twist lock mechanism is described.

Still further examples of the prior art are directed at methods and devices for securing a tracheotomy tube to prevent its inadvertent removal from the stoma formed in the patient's trachea. Examples include U.S. Pat. Nos. 5,819,734, 5,782,236, and 6,105,577. In each of these examples there are described methods for securing the tracheotomy tube using straps which extend around the neck of the patient and attach to a flange section covering the stoma opening in the patients trachea. The purpose of these devices is to hold the tracheotomy tube in place and allow for breathing or assisted ventilation without fear that the tracheotomy tube will be disturbed or in the case of assisted ventilation without fear that the supply line will be pulled out.

However, all of these devices suffer from several draw backs. Initially, in instances where the larynx has not been removed, the use of these tracheotomy tubes in conjunction with inflatable balloons adds to the complexity and difficulty for patients to talk. Further, many of these devices allow for forced respiration, but do not accommodate oxygenation in combination with normal breathing. Still further, the attachment means for these devices are cumbersome, prone to catching on clothing or disturbed while sleeping, and generally do not provide a neat solution to the oxygen supply problem. Accordingly, the present invention is directed at solving these and other problems associated with the known devices.

SUMMARY OF THE INVENTION

The present invention is directed to an implantable surgical apparatus including a first flange having an opening, a second flange having an opening, and a shaft having a lumen theretrough connecting the first and second flange openings, and for receiving and securing an oxygen supply line.

The present invention is also directed to an oxygen supply system including a first flange having an opening, a second flange having an opening, and a shaft having a lumen theretrough connecting the first and second flange openings and for receiving and securing an oxygen supply line. The oxygen supply system further includes a catheter inserted into the lumen of the shaft.

The present invention is also directed to a method of implanting a transtracheal stent. The method includes the steps of forming a stoma in the trachea of a patient and inserting the transtracheal stent into the stoma. The stent may also be secured to the patient through the use of sutures or other securing means. The implantation can be eased by a step of folding a first flange along the length of the stent, and a catheter can be inserted into the stent for supplying oxygen to the patient.

The various features of novelty which characterize the invention are pointed out in particularity in the claims annexed to and forming a part of this disclosure. For a better understanding of the invention, its operating advantages and specific objects attained by its uses, reference is made to the accompanying descriptive matter in which preferred embodiments of the invention are illustrated.

BRIEF DESCRIPTION OF THE DRAWINGS

For a more complete understanding of the invention, reference is made to the following description and accompanying drawings, in which:

FIG. 2 is an end view of a transtracheal stent according to the present invention;

FIG. 3 is a side view of transtracheal stent and catheter according to the present invention;

FIG. 4 is a side view of a catheter for use with a transtracheal stent according to the present invention; and FIG. 5 is a cross sectional view of a transtracheal stent according to the present invention.

DETAILED DESCRIPTION

Figure 1:
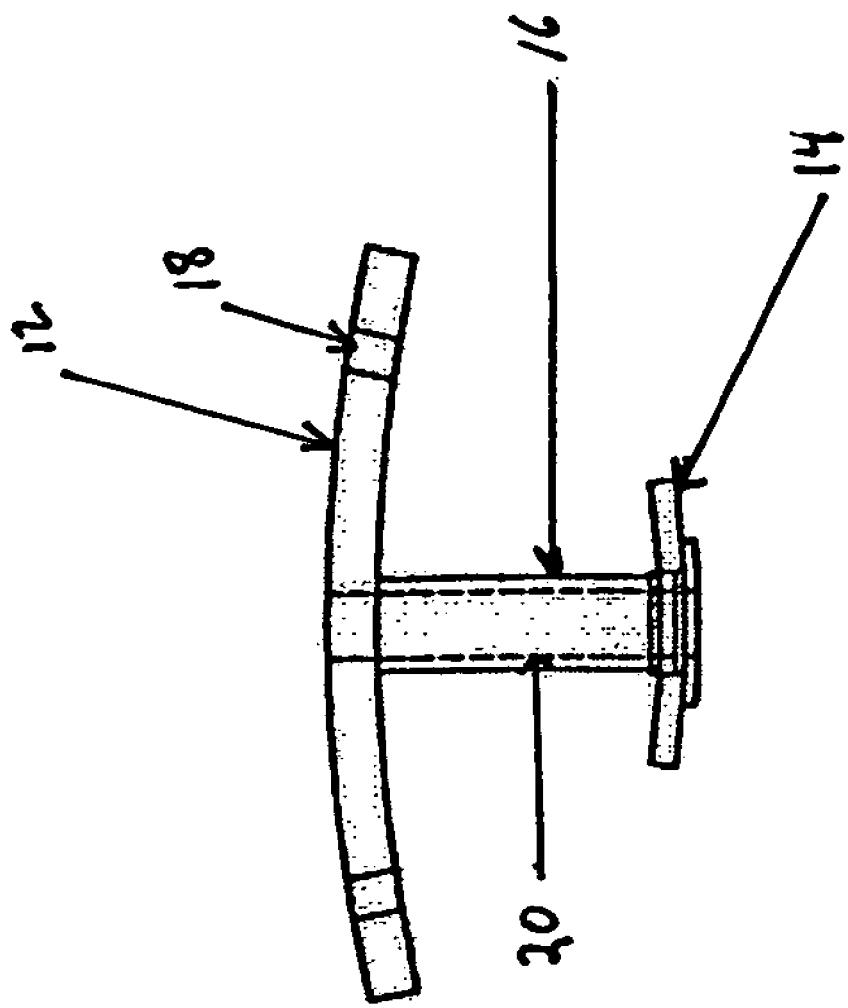
FIG. 1 is a top view of a transtracheal stent according to the present invention.

The present invention, which overcomes the shortcomings of the prior art is shown in FIG. 1. The transtracheal stent 10 is shown with a first flange 12, a second flange 14, and a connection tube 16. The tube 16 connects the two flanges and has a lumen 20 extending therethrough allowing for fluid communication from the first flange 12 to the second flange 14.

As shown in FIG. 1 both the first and second flanges have a curved shape. This curved shape opposes movement of the transtracheal stent after it has been implanted in a patient. The shape of the first flange 12 approximates the curvature of the patients neck, this has the benefit of avoiding unnecessary obtrusion from the patient's neck and providing for a relatively comfortable resting point of the device. The first flange may also be equipped with holes 18 for securing the stent 10 to the patient through the use of sutures or other surgical securing means. The curvature of the second flange 14 acts against the interior of the trachea to prevent the inadvertent removal of the stent 10 from the patient.

Further, the second flange 14 as shown in FIGS. 2 and 3 can be formed of two different thicknesses. As shown in FIG. 3, the distal ends of the second flange 14 can be formed with a lesser thickness 22 than that portion of the flange in the immediate vicinity of the tube 16. This difference in thickness allows for the distal ends of the device to be more easily folded along the tube 16 for implantation into the patient. Because of the curvature of the second flange 14, and the formation of the thinner distal ends, the second flange 14 resists being pulled in the direction of the first flange 12 or being ejected from the patient by coughing. Despite having a lesser thickness 22 than that portion of the second flange 14 in the immediate vicinity of the tube 14, the curvature of the flange and the formation of the distal ends help to prevent the second flange 14 from folding in the direction away from the first flange, and thereby assists in the securing of the tracheal stent in the patient.

The first and second flange 12, 14 may be so oriented that they are 90 degrees apart in relation to the tube 16. That is, in one embodiment of the present invention, the two flanges form an X when viewed from either end. This orientation is believed to further assist in securing the stent in the trachea of the patient.

A further advantage of the flanges is that they have a relatively low profile. The first flange is in one embodiment approximately 2.4 mm in thickness, while the second flange has a thickness of approximately 1.7 mm and where the distal ends of the second flange have a thickness of approximately 1 mm. Of course the flanges can be made to other thicknesses as desired to accommodate ease in implantation, and security once implanted in the patient as well as the materials used to form the device.

The transtracheal stent 10 is preferably made from medical grade silicone, but other materials could also be used without departing from the scope of the present invention. The medical grade silicone preferably has a hardness of 70 durometer for the first flange and 50 durometer for the remaining parts of the stent 10. By having the hardness of the first flange 12 be greater than that of the second flange 14, the stent is easier to implant into the patient. Further, having a harder first flange provides for a more robust stent that is less likely to be affected by the rigors of daily use, whereas a softer material would be more likely to flex and get caught in clothing and the like. Similarly, having a softer material for the second flange improves the feel of the stent 10 after implantation into the patient. The softer material allows the device to conform to the contours of the patient and provide a comfortable fit. Further, the use of a softer material on the second flange 14 allows for easier insertion and reduced insertion trauma for the patient because it is more flexible. It would be understood by those of skill in the art that the use of materials for the second flange 14 that are too soft would not be advantageous as this may allow the stent 10 to be pulled from the patients trachea or inadvertently ejected by coughing.

Another aspect of the present invention is the oxygen delivery catheter 24 shown in FIGS. 3 and 4. The catheter 24 is generally tubing which connects the stent 10 to an oxygen supply source 28. On the end which will be inserted into the stent 10, at a distance from the end approximately equal to the length of the stent 10 is a bushing 26. The bushing 26 prevents the catheter 24 from being inserted into the stent 10 beyond the desired distance. Another feature of the present invention is the lip 30 on the tube 16 side of the second flange 14 as shown in FIG. 5. The lip 30 also assists in preventing the catheter 24 from extending beyond the second flange 14 more than the desired distance. Yet another feature of the catheter is the bevel 32 on the end of the catheter 24 to be inserted into the stent 10. The bevel 32 helps to ease the insertion and retraction of the catheter 24 into and out of the stent 10. Extending from the end of the catheter 24 to be inserted into the stent 10 is a hood 36. The hood 36 assists in guiding the airflow of the oxygen away from the tracheal wall and down into the trachea of the patient. The hood 36 substantially eliminates the forcing of air against the tracheal wall and provides a more direct airflow route into the lungs of the patient.

A further feature of the catheter of the present invention is a pre-formed bend 34. The pre-formed bend 34 allows the wearer to have greater comfort when employing the device. By pre-forming the bend 34, there is less likelihood that the catheter 24 will kink and shut off the oxygen supply to the wearer. Similarly, the pre-formed bend 34 assists the wearer in allowing the supply lines to be run underneath of the clothing of the wearer and connect to the catheter at a convenient angle of attachment.

In one embodiment of the invention it is advantageous to insert the catheter 24 into the stent 10 so that the end of the catheter 24 extends approximately 1 mm beyond the surface of the second flange 14 of the stent 10. This distance serves two related purposes, initially, the 1 mm extension is not so great that large amounts of mucous and other debris collect on the stent 10 or catheter 24, and secondly, this distance allows for sloughing off of any mucous that does collect there. The mucous is sloughed off by the removal of the catheter 24 from the stent 10.

On the opposite end of the catheter 24 is a universal connector for insertion of standard oxygen tubing from the oxygen supply source. Accordingly, following implantation of the stent 10 in the patient, the catheter 24 can be inserted into the stent 10 until the bushing 26 rests against the end of the stent 10 and the oxygen supply can be started. To clean the stent 10 or the catheter 24, the catheter 24 can be removed from the stent 10. This removal action will have a cleaning effect on the end catheter 24, and the catheter can be further cleaned to ensure a good flow of oxygen to the patient.

A medical professional seeking to implant the stent 10 of the present invention will initially have to form a stoma in the trachea of the patient. Once the stoma is formed, the stent 10 can be inserted into the stoma. To ease insertion the second flange 14 is folded back along the tube 16 to minimize the profile of the stent 10. The stent 10 is inserted into the stoma of the patient and after reaching a certain point the second flange 14 will assume its original shape. At this point the stent 10 is secured in the stoma of the patient by the force applied by the curvature of the first and second flanges. If it is desirable, the medical professional can suture the first flange to the patient through the holes 18, or affix the flange through other means known to those skilled in the art. While the forgoing describe surgical implantation, the stent 10 may also lend itself to percutaneous implantation. This could be accomplished by using an apparatus such as the Cook percutaneous tracheostomy introducer, known to those of skill in the art, and which could be modified for use with the present invention.

While the present invention has been particularly shown and described in conjunction with preferred embodiments thereof, it will be readily appreciated by those of ordinary skill in the art that various changes may be made without departing from the spirit and scope of the invention. Therefore, it is intended that the appended claims be interpreted as including the embodiments described herein as well as all equivalents thereto.

The invention claimed is:

1. An implantable transtracheal surgical apparatus comprising:
    a first flange operable to be placed on the neck of a patient and having an opening therein said first flange having a first curvature;
    a second flange having an opening therein operable to be placed in the trachea of a patient and to secure the surgical apparatus therein said second flange having a second curvature opposite the first curvature; and
    a shaft having a lumen therethrough connecting said first and second flange openings, said shaft receiving and securing a transtracheal oxygen supply line.

2. The implantable surgical apparatus of claim 1, wherein the first and second flange are offset 90° from one another.

3. The implantable surgical apparatus of claim 1, further comprising through holes formed in the first flange for affixing the apparatus to the patient.

4. The implantable surgical apparatus of claim 1, wherein the second flange comprises a first and a second thickness, said second thickness portion being smaller than the first and being sufficiently flexible to assist in the implantation of the apparatus.

5. The implantable surgical apparatus of claim 1 further comprising a catheter inserted into the lumen for connection to an oxygen supply.

6. The implantable surgical apparatus of claim 5 wherein the distal end of the shaft includes a raised surface to prevent the insertion of said catheter beyond a desired point.

7. The implantable surgical apparatus of claim 5 wherein said catheter comprises a bushing larger in diameter than the lumen to prevent the insertion of the catheter beyond a desired point.

8. The implantable surgical apparatus of claim 5 wherein the catheter comprises a preformed bend.

9. The implantable surgical apparatus of claim 5 wherein the catheter comprises a beveled end for easing insertion into said shaft.

10. The implantable surgical apparatus of claim 1, wherein the first flange has a durometer hardness of about 70 and the second flange has a durometer hardness of about 50.

11. An implantable transtracheal oxygen supply system comprising:
    a first flange operable to be placed on the neck of a patient and having an opening therein said first flange having first curvature;
    a second flange having an opening therein operable to be placed in the trachea of a patient and to secure the surgical apparatus therein said second flange having a second curvature opposite the first curvature; and
    a shaft having a lumen therethrough connecting said first and second flange openings, said shaft receiving and securing a transtracheal oxygen supply line; and
    a catheter inserted into the lumen of said shaft.

12. The oxygen supply system of claim 11, wherein the first and second flange are offset 90° from one another.

13. The oxygen supply system of claim 11, further comprising through holes formed in the first flange for affixing the apparatus to the patient.

14. The oxygen supply system of claim 11, wherein the second flange comprises a first and a second thickness, said second thickness portion being smaller than the first and said second flange being sufficiently flexible to assist in the implantation of the apparatus.

15. The oxygen supply system of claim 11 wherein the distal end of the shaft includes a raised surface to prevent the insertion of said catheter beyond a desired point.

16. The oxygen supply system of claim 11 wherein said catheter comprises a bushing larger in diameter than the lumen to prevent the insertion of the catheter beyond a desired point.

17. The oxygen supply system of claim 11 wherein the catheter comprises a preformed bend.

18. The oxygen supply system of claim 11 wherein the catheter comprises a beveled end for easing insertion into said shaft.

19. The oxygen supply system of claim 11, wherein the first flange has a durometer hardness of about 70 and the second flange has a durometer hardness of about 50.

* * * * *